United States Patent [19]
Augustsson et al.

[11] Patent Number: 4,589,126
[45] Date of Patent: May 13, 1986

[54] RADIOTHERAPY TREATMENT TABLE

[76] Inventors: Nils E. Augustsson, Fasanvägen 2, S-232 00 Åkarp; Kjell O. T. Lindström, N. Skogsvägen 3, S-236 00 Höllviksnäs; Lars J. S. Mattsson, Persikevägen 43, S-223 55 Lund, all of Sweden

[21] Appl. No.: 693,059

[22] Filed: Jan. 22, 1985

[30] Foreign Application Priority Data

Jan. 26, 1984 [SE] Sweden ................ 8400414

[51] Int. Cl.$^4$ ................................. A61B 6/04
[52] U.S. Cl. ........................... 378/209; 378/205; 378/206
[58] Field of Search .............. 250/491.1; 378/205, 378/206, 209

[56] References Cited

U.S. PATENT DOCUMENTS 4,293,771 10/1981 Lescrenier ................ 378/206
4,344,498 8/1982 Lindfors .................... 180/168

FOREIGN PATENT DOCUMENTS 643668 6/1984 Switzerland .
2042217 1/1980 United Kingdom .
2068587 1/1980 United Kingdom .

Primary Examiner—Alfred E. Smith
Assistant Examiner—Jack I. Berman
Attorney, Agent, or Firm—Barnes, Kisselle, Raisch, Choate, Whittemore & Hulbert

[57] ABSTRACT

A radiotherapy treatment table is formed as a mobile table having a vertically movable patient supporting plane freely suspended at one end, all the wheels of said table being individually or jointly driven by a motor and turnable relative to the wheeled frame, a positioning and steering device being adapted to sense the position of the treatment table relative to a radiotherapy station and to drive and steer the table to a desired position in response to a measured actual position. The positioning and steering device may comprise sensors for inductively, optically or ultrasonically sensing the actual position of the table in an inductively, optically or ultrasonically marked coordinate system, and may also comprise a computer for controlling the positioning of the table and any preprogrammed movements relative to a treatment isocenter that may be necessary during the treatment.

11 Claims, 2 Drawing Figures

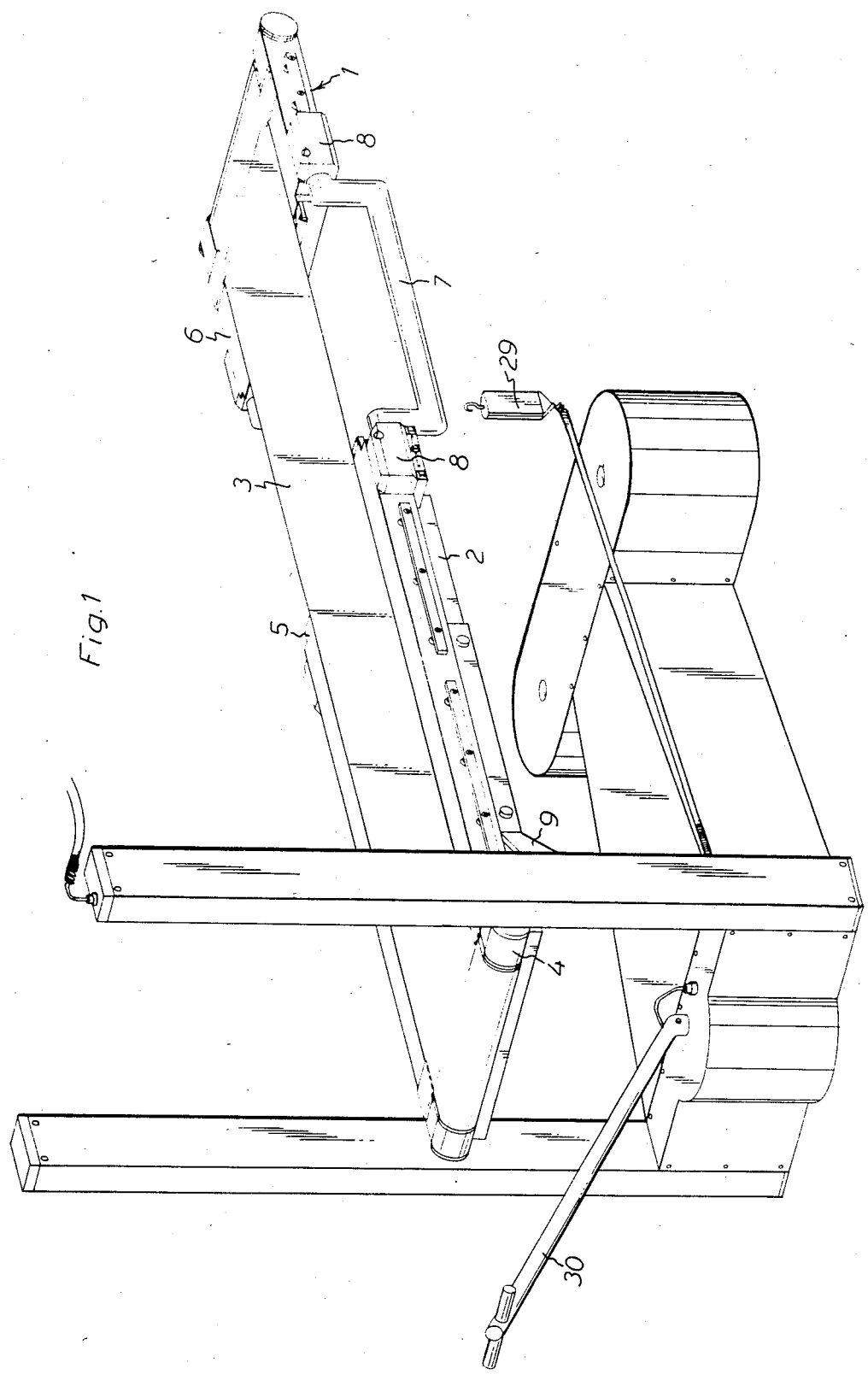

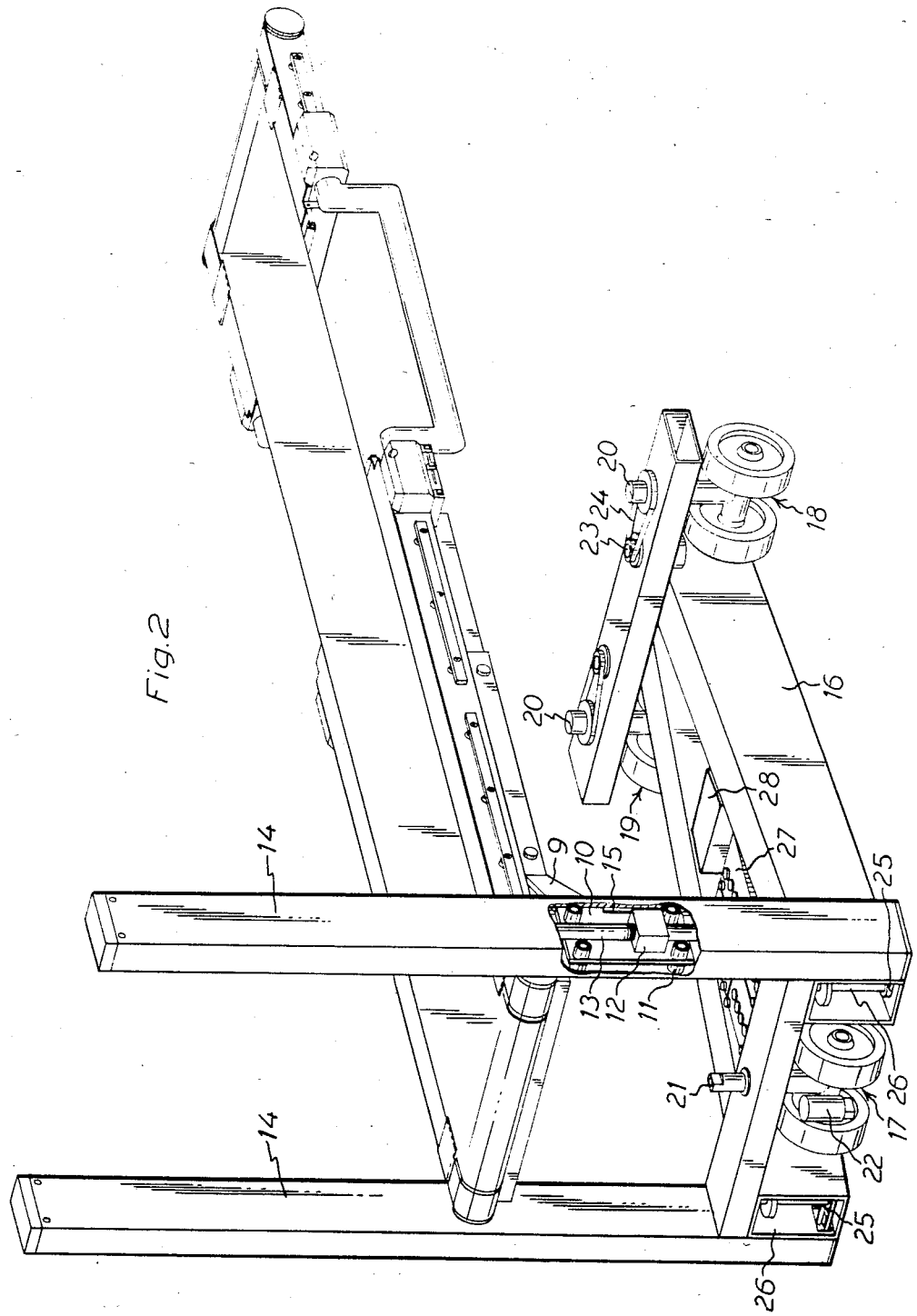

RADIOTHERAPY TREATMENT TABLE

In radiotherapy treatment of patients, it is imperative that the patient be held in correct position relative to the radiotherapy machine. The reason for this is that, in many cases, it should be possible to calculate and distribute the dose to the treatment area, which is absorbed by the patient, with a degree of accuracy of not more than ±5% in order to attain the expected treatment result without damaging the tissues outside the treatment area. For this reason, the only treatment tables which are being marketed at present are such tables as are isocentrically fixedly coupled with the radiotherapy machine because an uncertainty of at least ±3% lies already in the purely radiation technical and physical dose calculation. In view hereof, the margins for the individual dose planning and the correct positioning of the patient relative to the radiotherapy machine are very narrow. Thus, in connection with the treatment, an individual dose planning and mapping occurs in a separate simulator, and the patient must therefore be moved between the simulator and the actual radiotherapy machine. However, it was deemed necessary to accept this inconvenience to be able to obtain a satisfactory geometrical accuracy by utilising the isocentrically fixed coupling between the treatment table and the radiotherapy machine.

A great disadvantage of the conventional technique is, however, that positioning of the patient is time-cunsuming, and that the radiotherapy machine therefore unavoidably is idle during the long positioning periods. In order to reduce to some extent the setting-up times during exchange of patients in a radiotherapy station, it has been proposed to use exchangeable table tops transportable on separate carriages, or exchangeable tables running on rails so that the capacity of the treatment equipment can be increased and the repositioning work in connection with simulation in a separate simulator can be avoided. In this prior art technique, the coupling and uncoupling of the exchangeable table tops or the positioning of the exchangeable tables is fraught with considerable difficulties. Another disadvantage of the known radiotherapy tables is that they often do not permit so-called dynamic radiotherapy treatment, except when specially equipped standard tables are utilised. Because of the play occurring in these known tables in respect of coordinate movements, dynamic radiotherapy treatment usually can be carried out only in a single treatment plane, i.e. the only possibility is to rotate the machine around a patient, thereby to reduce damage to adjacent tissue.

Originally, conventional tables were railborne to provide for exact movements in the radiation plane. Rails mounted on the floor have greatly reduced vertical table movement, and with rails mounted in the ceiling, the great overhang has resulted in shakiness and sway. Furthermore, movement on rails in the radiation plane as the first coordinate greatly hampers isocentric horizontal movement of the table top, the centre of rotation of which lies outside the isocentre.

Conventional tables rotating isocentrically in the horizontal plane have either been suspended from the ceiling or mounted in the floor. Tables suspended from the ceiling give large overhangs and great distances, resulting in sway and shakiness. On the other hand, they provide for considerable vertical movements. Practically all isocentrically fixed tables are secured in the floor. In order to obtain a large vertical movement with a centre line column, a deep pit must be provided in the floor (2-3 m). With the isocentric movement as the first coordinate, difficulties are encountered with the parallel movement in the radiation plane. In conventional tables, the second coordinate from the point of attachment is the vertical movement. In most constructions, the vertical movement is directly under the centre line of the table top, so far from the isocentre that the radiation therapy machine will go free when radiation is applied from below. In order to achieve a great lifting height, it is necessary either to provide a deep pit in the floor or a co-rotating lifting column laterally of the table top.

The transverse movement of the table top usually is the third coordinate. Its direction thus rotates with the isocentric movement and is parallel to the radiation plane only in zero position. This is the principal practical shortcoming of conventional tables. In order to establish an acceptable stability, this transverse movement is highly restricted (maximum ±25 cm). Already at isocentre angles of 5°, unacceptable displacements of the patient relative to the radiation plane are obtained at lateral movements exceeding 10-15 cm. To compensate for this, a fourth coordinate is required, i.e. longitudinal movement of the table top. To enable adjustment of the transverse movement by more than is allowed by the linear coordinate, most tables have a fifth coordinate, rotation about the lifting column (cf. for instance R. F. Mould, Medical Physics Handbooks 7, Radiotherapy Treatment Planning, Adam Hilger Ltd., Bristol, Great Britain, 1981, p. 9, FIG. 4). In some tables, the isocentric movement is coupled in synchronism with the rotation of the column, but the combination movement requires compensation in the longitudinal coordinate of the table top, and this movement is not automated in any standard table (for dynamic therapy utilising transverse movement, such coupling must be provided). The horizontal movement pattern or conventional isocentrically fixed tables thus requires four separate coordinate movements for correct setting of the treatment areas.

For these reasons, there is a need for a construction by which all transport movements and all requisite correction movements can be effected without repositioning of the patients upon exchange of patients in a radiotherapy machine. It therefore is one of the objects of the present invention to satisfy this need.

Another object of the present invention is to permit quicker and more accurate positioning of a patient by means of a new type of radiotherapy treatment table. Another object of this invention is to permit so-called dynamic radiotherapy for which the patient is moved relative to the radiotherapy machine which besides and if necessary executes the conventional rotational or pivotal movements.

The present invention is based upon the insiqht that a treatment table, to be efficient and accurate, should be movable relative to the radiotherapy machine in an exactly controllable manner. The present invention therefore provides a treatment table which has a vertically movable patient supporting plane mounted on a frame and adapted to support and position the patient during treatment. This patient supporting plane may be provided, in known manner, with a patient supporting surface in the form of a conveyor belt mounted on and supported by said supporting plane for positioning the patient in the longitudinal direction of the table. However, the characteristic feature of the treatment table according to the present invention is that the patient supporting plane is mounted at one end on a column on a mobile wheeled frame for the table, and at its other end is freely suspended, the column comprising a lifting device for raising and lowering of the patient supporting plane; that all the wheels of the wheeled frame are mounted on wheel holders rotatable relative to the wheeled frame and are individually or jointly motor-driven; and that the table has a positioning and steering device adapted to sense the position of the treatment table relative to the radiotherapy station and to drive and steer the table, in response to a measured actual position, into a desired position.

The table preferably may be provided with a manual driving and steering device for rough adjustment of the table position relative to the radiotherapy station.

According to the invention, it is especially advantageous if the positioning and steering device comprises drive means for setting the rotatable wheel holders to control the direction of travel of the wheeled frame, and control means for controlling the travelling distance of the wheeled frame in the set direction. The positioning and steering device preferably also comprises sensors for inductive, optical or ultrasonic sensing of the actual position of the table in an inductively, optically or ultrasonically marked coordinate system. In this manner, it is possible to zeroise the positioning and steering device in such a coordinate system and then let a computer included in said positioning and steering device control the positioning of the table and any preprogrammed movements relative to a treatment isocentre that may be necessary during the treatment.

The invention makes it possible to provide an exact geometric operation of the treatment table, whereby essential advantages in practical radiotherapy are obtained. Thus, the need for repositioning of the patient has been eliminated.

If the wheels are mounted in pairs and suspended according to the same principle as the nosewheels of an airliner, the entire treatment table can be moved without necessitating repositioning of the patient himself in relation to the patient supporting surface. With known stationary and isocentrically movable treatment tables, all misalignment of the patient with respect to the radiotherapy machine must be adjusted by repositioning the patient on the patient supporting surface proper. By microcomputer-based control of the wheels, any desired movement in the plane is obtainable, i.e. both translatory and rotational movements. At the same time, also the lifting device for the patient supporting plane can be connected to the microcomputer so that the supporting plane can also be automatically raised and lowered.

By designing the treatment table as a mobile table, other advantages from the viewpoint of patient manipulation are obtained. Vertical movement can be organised such that the plane can be lowered to a level of about 50 cm from the floor so that ambulatory patients can comfortably and without the assistance of a stool sit down on the patient supporting plane. Furthermore, the treatment table can be moved up to a bed, and the patient supporting plane is then adjusted to the suitable height, for example about 60 cm, for transferring bed-ridden patients with the aid of some type of sliding board.

By using a greater number of treatment tables than radiotherapy machines patient treatment can be made much more efficient in that the patients can be moved, without repositioning, from a simulator to the radiotherapy machine.

A further considerable advantage of the table according to the present invention resides in the fine adjustment of the patient relative to the radiotherapy machine. Thus, fine adjustment of a patient's position in relation to a patient supporting surface is extremely difficult, especially if the patient has been deposited in an oblique position on the supporting surface. If the patient is placed correctly, i.e. symmetrically in the lateral sense, most of the marks on the patient's skin, especially on the stomach and at the sides, will inevitably be affected, and it is difficult to attain the extreme precision which is sought in critical cases and which, on technical grounds, is required for the correct utilisation of existing position checking systems. In conventional (non-dynamic) isocentric treatment technique, in particular, maximum accuracy in the patient's position is required. These difficulties have been eliminated by the mobile treatment table according to the present invention in that it is possible first to position the patient longitudinally on the patient supporting surface and then to position the table in the longitudinal, lateral and rotational senses (about the vertical axis of rotation) until agreement is obtained between, for example, laser light indications and markings on the patient (and the patient fixture). After that, the coordinate system of the table is zeroised, and via the microcomputer the movements of the table and the absolute position can be indicated both in parallel and in circular coordinates for the setting of the treatment areas concerned. All movements in the horizontal plane are effected by means of the wheels of the mobile table, and the need for a mechanical coordinate plane, of the type utilised in prior art equipment, has been eliminated.

As mentioned above, the table according to the invention can be used also for dynamic therapy. By the term dynamic therapy is meant not only complete stereotactic treatment but also, and above all, radiation during movement of the different parameters of the treatment machine and during simultaneous table movements to supplement the angles of attack of the radiation direction. Thus, in dynamic therapy exceptionally great demands are made on the table movements relative to the radiotherapy machine. The exact position-coupled operation obtainable with a mobile treatment table according to the present invention makes it possible to establish remote control of the table movements in response to the contemplated dynamic therapy.

A further advantage of the table according to the present invention is that any play that may develop in the lifting device will be less important because the significance of wear resulting in such play is eliminated by the heavy unilateral load caused by the freely suspended end of the patient supporting plane. If the wheel drive takes place at a high transmission ratio, the feedback position checking signal may be used to eliminate the effect of wear-induced play on the movement of the table in the plane. The exact wheel drive with feed-back of position indicating signals in the table according to the present invention also eliminates the mechanical system usually to be found in the supporting column of the patient supporting surface, by which lateral and/or longitudinal displacement of the entire patient supporting surface in the selected vertical plane is made possible. This mechanical system is bulky and also highly susceptible to wear resulting in play so that already an insignificant wear can give an error of several centimeters at the ends of the patient supporting surface.

In a treatment table according to the present invention, the transport functions and all requisite movements in the horizontal plane are carried out by means of the supporting wheels and their drive with feed-back of a position checking signal via a microcomputer to be able fully to utilise this exact positioning in the coordinate system of the horizontal plane, an absolutely planar base or floor is required for the treatment table. However, builders are familiar with the requisite technique for making a floor which is sufficiently planar, and in the utilisation of this invention it is thus possible to move the treatment table in the horizontal plane with such exactitude that normally no adjustment of the distance from the radiation source to the patient is required.

A system which may be used and at presently is preferred as a steering system in the treatment table of the invention is described in U.S. Pat. No. 4,344,498 and GB-A-No. 2,068,587 which are included in this specification by reference.

Besides having access to a planar floor or base, no special alterations are required in the premises where the radiotherapy machine is installed. Thus, the present invention does not require, for example, deep pits in the floor to provide for sufficient vertical movement.

The treatment table according to the present invention can be used for a great many applications. Thus, the table can be used both for conventional radiotherapy and for dynamic therapy, and also for nuclear medical treatments. The table can also be used as an operating table, especially for intraoperative radiation treatment, in which case the movability of the table is utilised for permitting operative exposure of the tumour in a special sterile room, whereupon the patient, while still lying on the table, is transported to the radiation machine. If during this transport, and also during the radiation treatment, the patient and the operating area are covered with, for example, a sterile "MYLAR" ® foil, the radiation treatment room need not be sterilised, as is required of known treatment tables which are stationary in the radiation treatment room. The invention thus makes it possible, in such cases, considerably to increase the treatment capacity.

An embodiment of a treatment table according to the present invention will be described in more detail below, reference being had to accompanying drawings in which FIGS. 1 and 2 are perspective views with and without, respectively, cover plates and certain component details.

Thus, FIG. 1 shows a treatment table which comprises a patient supporting plane 1 having a frame 2 which supports a conveyor belt 3 travelling over guide pulleys 4. Within parts of its length, the conveyor belt rests upon base surfaces 5, 6 on the frame 2. Between the two base surfaces 5 and 6, the conveyor belt 3 extends freely over a short distance. The frame 2 has two yoke-shaped frame members 7 (only one is shown) which are pivotally mounted in bearing boxes 8 for adjustment in different positions relative to the remainder of the frame to facilitate radiotherapy treatment.

At one end, the frame 2 is rigidly connected with brackets 9 (only one is shown) which are rigidly connected with or formed integrally each with one plate 10 (FIG. 2) having supporting rollers 11. The plate is provided with a nut 12 which either is formed integrally with the plate or rigidly anchored thereon for engagement with a rotatable screw 13 for vertical adjustment in a column 14. The column 14 has in one narrow long side a vertically extending slit 15 in which the bracket 9 and the plate 10 travel.

The columns 14 are rigidly assembled with a wheeled frame 16 having three pivotal pairs of wheels 17, 18, 19 each mounted on a rotatable shaft 20, 21. One wheel of each pair of wheels is drivable by means of a motor 22. The other wheel of said pair of wheels may serve as a free-running measuring wheel. At least the shafts 20, and preferably also the shaft 21, are connected with a drive motor 23, for example by means of a toothed belt transmission 24, so that the different pairs of wheels can be swung for steering the table.

For vertical movement of the treatment table, each screw 13 is provided at its lower end with a belt pulley for engagement with a transmission belt 25 engaging a belt pulley on a shaft 26. The shafts 26 on either side of the wheeled frame are then coupled in a manner not shown to a common drive motor for joint rotation of the two screws when the table 1 is raised or lowered.

The wheeled frame 16 may be provided with powersupplying accumulators 27 and with a computer 28 forming part of the table positioning and steering device.

As mentioned above, one wheel of either pair of wheels may be a measuring wheel comprising a transducer for feeding back driving information to the computer 28 in connection with the control of the table position. The computer also is connected to sensing means (not shown) for optical, inductive or ultrasonic sensing of the position of the table in a coordinate system.

As will appear from FIG. 1, a manual driving and steering device having a hand operated control panel 29 is also included.

Finally, it appears from FIG. 1 that the shaft 21 may be connected with a drawing and steering bar 30 for manually moving the table, if this is desired.

What we claim and desire to secure by Letters Patent is:

1. A radiotherapy treatment table which has a vertically movable patient supporting plane mounted on a frame and adapted to support and position the patient during treatment, characterized in that the patient supporting plane is mounted at one end on a column on a mobile wheeled frame for the table, and at its other end is freely suspended, the column comprising a lifting device for raising and lowering of the patient supporting plane; that all the wheels of the wheeled frame are mounted on wheel holders rotatable relative to the wheeled frame and are motor-driven; and that the table has a positioning and steering device which senses the position of the treatment table relative to a radiotherapy station and drives and steers the table, in response to a measured actual position, into a desired position.

2. A table as claimed in claim 1, characterized in that all the wheels of the wheeled frame are individually motor-driven.

3. A table as claimed in claim 1, characterized in that all of the wheels of the wheeled frame are jointly motor driven.

4. A table as claimed in claim 1, characterized in that it comprises a manual driving and steering device for rough adjustment of the table position relative to the radiotherapy station.

5. A table as claimed in claim 1 or 4, characterized in that the positioning and steering device comprises drive means for rotating and setting the rotatable wheel holders to control the direction of travel of the wheeled frame, and control means for controlling the travelling distance of the wheeled frame in the set direction.

6. A table as claimed in claim 5, characterized in that the positioning and steering device also comprises sensors for inductive, sensing of the actual position of the table in an inductively, marked coordinate system.

7. A table as claimed in claim 6, characterized in that the positioning and steering device comprises a computer for controlling the positioning of the table and any movements, preprogrammed relative to a treatment isocentre, that may be necessary during the treatment.

8. A table as claimed in claim 3, characterized in that the positioning and steering device also comprises sensors for optical sensing of the actual position of the table in an optically marked coordinate system.

9. A table as claimed in claim 8, characterized in that the positioning and steering device comprises a computer for controlling the positioning of the table and any movements, programmed relative to a treatment isocentre, that may be necessary during the treatment.

10. A table as claimed in claim 5, characterized in that the positioning and steering device also comprises sensors for ultrasonic sensing of the actual position of the table in an ultrasonically marked coordinate system.

11. A table as claimed in claim 10, characterized in that the positioning and steering device comprises a computer for controlling the positioning of the table and any movements, preprogrammed relative to a treatment isocentre, that may be necessary during the treatment.

* * * * *